(12) United States Patent
Jennings et al.

(10) Patent No.: US 9,539,392 B2
(45) Date of Patent: Jan. 10, 2017

(54) AUTO-INJECTOR

(75) Inventors: Douglas Jennings, Herts (GB);
Thomas Kemp, Hertfordshire (GB);
Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 799 days.

(21) Appl. No.: 13/994,883

(22) PCT Filed: Dec. 21, 2011

(86) PCT No.: PCT/EP2011/073510
§ 371 (c)(1),
(2), (4) Date: Jun. 17, 2013

(87) PCT Pub. No.: WO2012/085029
PCT Pub. Date: Jun. 28, 2012

(65) Prior Publication Data
US 2013/0274671 A1    Oct. 17, 2013

Related U.S. Application Data

(60) Provisional application No. 61/432,239, filed on Jan. 13, 2011.

(30) Foreign Application Priority Data

Dec. 21, 2010 (EP) .................................... 10196075

(51) Int. Cl.
*A61M 5/20* (2006.01)
*A61M 5/24* (2006.01)
(Continued)

(52) U.S. Cl.
CPC .............. *A61M 5/20* (2013.01); *A61M 5/24* (2013.01); *A61M 5/1452* (2013.01);
(Continued)

(58) Field of Classification Search
CPC .............. A61M 5/2053; A61M 5/3204; A61M 2005/206; A61M 5/46; A61M 5/326; A61M 2005/208; A61M 5/20; A61M 5/24; A61M 2005/2488; A61M 5/1452; A61M 5/3213; A61M 2005/31588; A61M 2205/6054; A61M 2205/6072

See application file for complete search history.

(56) References Cited

U.S. PATENT DOCUMENTS 4,833,384 A * 5/1989 Munro ................ A61M 5/1452
128/DIG. 1
4,976,701 A * 12/1990 Ejlersen .................. A61M 5/24
206/365

(Continued)

FOREIGN PATENT DOCUMENTS

EP    2253348    11/2010
FR    2654938    5/1991

(Continued)

OTHER PUBLICATIONS

International Search Report for Int. App. No. PCT/EP2011/073510, completed Mar. 2, 2012.
(Continued)

*Primary Examiner* — Imani Hayman
*Assistant Examiner* — Hamza Darb
(74) *Attorney, Agent, or Firm* — Fish & Richardson P.C.

(57) ABSTRACT

The invention relates to a front-end device of an auto-injector (A) for administering a dose of a liquid medicament, comprising of a support sleeve with a first screw thread adapted to engage a housing of a back-end device of the auto-injector (A) to attach the front-end device to the back-end device and an outer sleeve mounted onto a support sleeve of the front-end device by a second screw thread, wherein the front-end device is adapted to receive a syringe with an injection needle and a barrel containing the dose of the medicament and wherein the direction of rotation of the first screw thread is opposite to the direction of rotation of the second screw thread.

13 Claims, 8 Drawing Sheets

(51) Int. Cl.
 *A61M 5/145* (2006.01)
 *A61M 5/32* (2006.01)
(52) U.S. Cl.
 CPC ..... *A61M 5/3204* (2013.01); *A61M 2005/208* (2013.01); *A61M 2005/2488* (2013.01)

(56) References Cited

U.S. PATENT DOCUMENTS

| | | | |
|---|---|---|---|
| 6,171,276 B1 * | 1/2001 | Lippe | A61M 5/20 128/DIG. 1 |
| 2002/0095120 A1 | 7/2002 | Larsen et al. | |
| 2008/0228147 A1 * | 9/2008 | David-Hegerich | A61M 5/326 604/198 |
| 2011/0004165 A1 * | 1/2011 | Iio | A61M 5/20 604/197 |

FOREIGN PATENT DOCUMENTS

| | | |
|---|---|---|
| GB | 2445090 | 6/2008 |
| JP | 2001/511404 | 8/2001 |
| JP | 2005/516646 | 6/2005 |
| JP | 2010/535558 | 11/2010 |
| WO | 99/44657 | 9/1999 |
| WO | WO2009/125582 | 10/2009 |
| WO | WO2010/073452 | 1/2010 |

OTHER PUBLICATIONS

Japanese Office Action in Application No. 2013/545337, dated Nov. 10, 2015, 10 pages, including English translation.

* cited by examiner

AUTO-INJECTOR

CROSS REFERENCE TO RELATED APPLICATIONS

The present application is a U.S. National Phase Application pursuant to 35 U.S.C. §371 of International Application No. PCT/EP2011/073510 filed Dec. 21, 2011, which claims priority to European Patent Application No. 10196075.5 filed Dec. 21, 2010 and U.S. Provisional Patent Application No. 61/432,239 filed Jan. 13, 2011. The entire disclosure contents of these applications are herewith incorporated by reference into the present application.

TECHNICAL FIELD

The invention relates to a front-end device of an auto-injector for administering a dose of a liquid medicament adapted to engage a housing of a back-end device of the auto-injector to attach the front-end device to the back-end device, wherein the front-end device is adapted to receive a syringe with an injection needle and a barrel containing the dose of the medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved front-end device of an auto-injector for administering a dose of a liquid medicament adapted to engage a housing of a back-end device of the auto-injector to attach the front-end device to the back-end device, wherein the front-end device is adapted to receive a syringe with an injection needle and a barrel containing the dose of the medicament.

The object is achieved by a front-end device according to claim 1.

Preferred embodiments of the invention are given in the dependent claims.

In the context of this specification the term proximal refers to the direction pointing towards the patient during an injection while the term distal refers to the opposite direction pointing away from the patient. The terms "clockwise" and "counter-clockwise" in the context of this specification refer to senses of rotation with the auto-injector pointing with its distal end towards the observer.

According to the invention, a reusable front-end device of an auto-injector for administering a dose of a liquid medicament comprises a support sleeve with a first screw thread adapted to engage a housing of a back-end device of the auto-injector to attach the front-end device to the back-end device and an outer sleeve mounted onto a support sleeve of the front-end device by a second screw thread. The front-end device is adapted to receive a syringe with an injection needle and a barrel containing the dose of the medicament. The direction of rotation of the first screw thread is opposite to the direction of rotation of the second screw thread.

Before the injection is preformed, a pre-filled syringe is loaded into the front-end device. The front-end device is then attached to the back-end device via the first screw thread. Subsequently, the protective outer sleeve is removed from the support sleeve. The first and the second screw thread mounting the outer sleeve are arranged in a manner that allows the user to grasp the outer sleeve of the front-end device and attach the back-end device to the front-end device by continuously rotating the front-end device relative to the back-end device in one direction. When support sleeve is screwed all the way in and the first screw thread bottoms out, the user continues to rotate the front-end device relative to the back-end device in the same direction to detach the outer sleeve from the support sleeve, whereby the outer sleeve disengages the second screw thread of the support sleeve. The auto-injector is thus particularly simple and intuitive to assemble before an injection is performed.

Both the back-end device and the front-end device of the auto-injector are designed to be used in a plurality of injections. The only single-use element is the pre-filled syringe that is inserted into the front-end device before assembly of auto-injector. This allows for the reduction of production costs and minimizes waste.

According to a possible embodiment of the invention, a syringe retainer adapted to receive the pre-filled syringe is slidably arranged with respect to the support sleeve and may be axially translated between a first position with the needle covered inside the support sleeve and a second position with the needle exposed for injection. An assembly lock comprises a second inward projection that is arranged to latch to a first flange of the syringe retainer to prevent an axial translation of the syringe retainer in the first position (I) towards the second position (II) when the outer sleeve is mounted onto the support sleeve. The outer sleeve is arranged to abut against the assembly lock in a radial direction to translate the assembly lock radially inwards, so that the second projection engages the first flange to axially affix the syringe retainer. The pre-filled syringe may thus be conveniently inserted into the front-end device while the outer sleeve is mounted on the support sleeve. Removal of the outer sleeve from the support body removes the axial constraint, so that the syringe retainer with the pre-filled syringe mounted thereto is axially translatable with respect to the support sleeve from the first position into the second position to expose the injection needle.

Preferably, an annular rib is formed to the support sleeve to limit the axial translation of the syringe retainer in the proximal direction when the syringe retainer is retained in the second position. In the second position, the injection needle protrudes from a proximal end of the front-end device. The annular rib is arranged so as to limit the length by which the injection needle protrudes from the front-end device and hence a maximal penetration depth of the injection needle. The penetration depth may preferably be adapted for a subcutaneous or intra-muscular injection.

Alternatively, the penetration depth of the injection needle may be controlled by the re-usable back-end device of the auto-injector.

According to another possible embodiment of the invention, a support collar separates the first screw thread from the second screw thread. A latch formed to the outer sleeve latches to the support collar of the support sleeve to initially prevent a relative rotation between the outer sleeve and the support sleeve. The outer sleeve is thus prevented from disengaging the second screw thread when the front-end device is screwed to the back-end device by rotating the outer sleeve relative to the housing of the back-end device.

Preferably, a drive dog is slidably mounted to the support collar. The drive dog is arranged to abut against the latch and arranged to be engaged by the housing of the back-end device attached to the support sleeve via the first screw thread. The latch is adapted to be translated by the drive dog engaged by the housing, so that the latch disengages from the support collar. When the support sleeve is screwed to the housing, the housing abuts against the drive dog and translates the drive dog proximally, whereby the latch rotationally affixing the outer sleeve to the support sleeve is released. Thus, the removal of the outer sleeve is prevented until the front-end device is firmly attached to the back-end device.

According to yet another possible embodiment of the invention, the outer sleeve is connected to at least one clamp arm adapted to clamp to a needle cap covering the injection needle. The pre-filled syringe is inserted into the front-end device with its injection needle covered by the protective needle cap when the auto-injector is prepared for an injection. The clamp arms clamp to the needle cap and allow for a removal of the needle cap by pulling the outer sleeve off the support sleeve. Thus, the chance of the user incurring an accidental needle stick injury when loading the syringe into the front-end device and assembling the auto-injector is minimized.

The clamp arm may be biased by a clamp spring radially inwards to retain the needle cap within the outer sleeve when the outer sleeve is detached from the support sleeve. The needle cap is retained in the outer sleeve in a manner that facilitates the re-attachment of the needle cap to the syringe. After the injection is completed, the outer sleeve is re-attached to the support sleeve, whereby the needle cap reengages the syringe to cover the used injection needle. Thus, the injection needle of the syringe is covered after the injection and the emptied syringe may safely be removed from the front-end device.

According to yet another possible embodiment of the invention, a needle shroud adapted to rest on the skin of the patient is slidably arranged with respect to the support sleeve. In particular, the needle shroud may be arranged to be pushed against the skin to axially translate the needle shroud into a retracted position. The needle shroud comprises an extension arm adapted to communicate the axial displacement of the needle shroud to the back-end device of the auto-injector and thus indicates to the back-end device if the auto-injector is properly placed onto the skin of the patient. The back-end device may have means to prevent an activation of an injection mechanism if the needle shield is not positioned in the retracted position and thus is not in contact with the skin of the patient. Therefore, a premature or inadvertent activation of the injection mechanism wasting the medicament and/or compromising safety is avoided.

According to the invention, the auto-injector for administering a dose of a liquid medicament comprises
   a substantially tubular and reusable front-end device as described herein before and
   a reusable back-end device comprising
      a housing,
      a plunger connected to or adapted to engage a stopper providing a fluid tight seal for a distal end of the barrel,
      a motor for displacing the plunger.

The front-end device is attached to the housing via the first screw thread and outer sleeve is mounted onto a support sleeve by the second screw thread. The direction of rotation of the first screw thread is opposite to the direction of rotation of the second screw thread. The auto-injector combines the aforementioned advantages of the re-usable front-end device with the benefits of having a re-usable back-end device releasably attached thereto.

According to a possible embodiment of the invention, the outer sleeve is arranged to release an assembly lock upon removal of the outer sleeve from the support sleeve. Upon release, the assembly lock is capable of locking the support sleeve to the housing so as to prevent a relative rotation between the support sleeve and the housing. Hence, the front-end device is prevented from being detached from the back-end device while the injection is performed. The assembly lock is unlocked by re-attaching the outer sleeve to the support body, so that the auto-injector may be disassembled after the injection is completed.

Preferably, the assembly lock comprises a first locking pin and a second locking pin. The first locking pin protrudes into a first orifice formed into the support sleeve and the second locking pin protrudes through a second orifice formed into the support sleeve and into a third orifice formed into the housing to prevent the relative rotation between the support sleeve and the housing. The outer sleeve is arranged to abut against the first locking pin in the radial direction to retain the assembly lock in a position, in which the second pin does not protrude into the third orifice and thus allows for a detachment or attachment of the front-end device from the back-end device. In particular, the user is forced to re-attach the outer sleeve to the support sleeve before the auto-injector may be disassembled before the emptied syringe may be removed from the front-end device. As the re-attachment of the outer sleeve covers the injection needle, protection from accidental needle stick injuries is provided.

According to yet another possible embodiment of the invention, an interlock switch is arranged within the back-end device capable of detecting the axial displacement of the needle shroud slidably arranged with respect to the support sleeve and adapted to rest on the skin of a patient receiving an injection. The interlock switch thus detects if the needle shroud is in contact with the skin of the patient and is preferably part of a mechanism that prevents an activation of the motor of the back-end device. The motor of the back-end device may be an electric motor, a spring driven or pneumatic motor or another drive means.

According to yet another possible embodiment of the invention, the back-end device further comprises a sensor unit for detecting actual parameters of the injection, a memory unit for storing user related data and/or specification parameters and a means to provide a visual, acoustical and/or haptic feedback to the user of the auto-injector. The stored user related data may be used for compliance monitoring and thus be used to monitor the frequency of the injections that are the patient performs. In particular when the patient is on a medication, the proper dosage and and/or frequency of the administration may be supervised The sensor unit is capable of detecting actual parameters, like the type of medicament or drug contained in the pre-filled syringe in particular by means of radio frequency identification (RFID) or barcode reading. This allows for, amongst others, an automatic configuration of the auto-injector to properties of the medicament. For example, the penetration depth of the injection needle may be automatically adapted to a depth as required by the medicament. Furthermore, a set of device specification parameters may be stored in the memory unit. The specification parameters stored in the memory unit may be compared with actual parameters determined by the sensor unit during use of the auto-injector. For example, a current measured during the needle insertion process is characterized by the force needed to insert the injection needle into the skin. If the measured current is out of specification, the back-end device detects an incorrect use of the auto-injector and aborts the injection. Another possible application includes comparing the initial position of the stopper with a corresponding specification parameter at the beginning of the injection. If the position of stopper is out of specification, the back-end device detects that a used and empty syringe is loaded to the front-end device and disable the injection mechanism to prevent injuries. The auto-injector may fail to operate when no syringe is inserted into the syringe retainer.

Visual means of the back-end device may in particular comprise a display, preferably a liquid crystal display (LCD), that shows the injection progress, injection completion, historical user data and/or drug properties, like an expiry date. The display may show messages to remind the patient to take his medicament, specification parameters, an operation mode and/or the type of the medicament contained in the pre-filled syringe. Additionally or alternatively, the back-end device may comprise adequate means to provide an acoustic and/or haptic feedback to the patient and/or the user of the auto-injector.

According to yet another possible embodiment of the invention, the back-end device further comprises an encoder sensor capable of determining the position of the plunger. Detection of the position of the plunger may be used to control the translation speed of the plunger. In particular, the translation speed of the plunger may be adapted to the different phases of the drug delivery comprising the needle insertion phase, the expelling of the medicament and the needle retraction phase. In particular, the encoder sensor may be arranged as a rotary or linear encoder capable of detecting the position of the plunger and converting the detected position to a corresponding digital or analogue signal.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
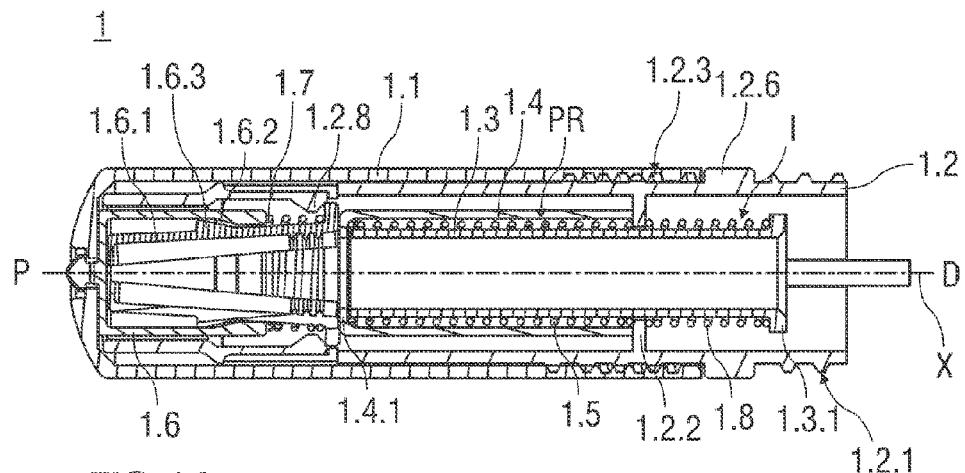
FIGS. 1A and 1B show sectional views of a reusable front-end device of an auto-injector according to a first embodiment of the invention before a pre-filled syringe is loaded into the front-end device.
Figure 1B:
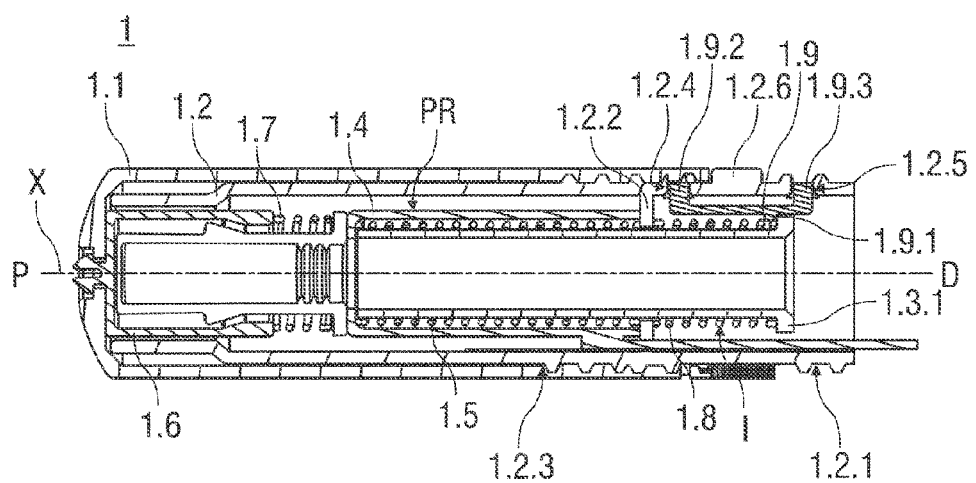

FIGS. 1A and 1B show sectional views of a reusable front-end device 1 of an auto-injector A that is adapted to receive a syringe 2. The front-end device 1 shown in FIGS. 1A and 1B is empty; the syringe 2 that is pre-filled with a dose of a medicament may be inserted into the front-end device 1 before an injection through a distal end of the front-end device 1.

Figure 9A:
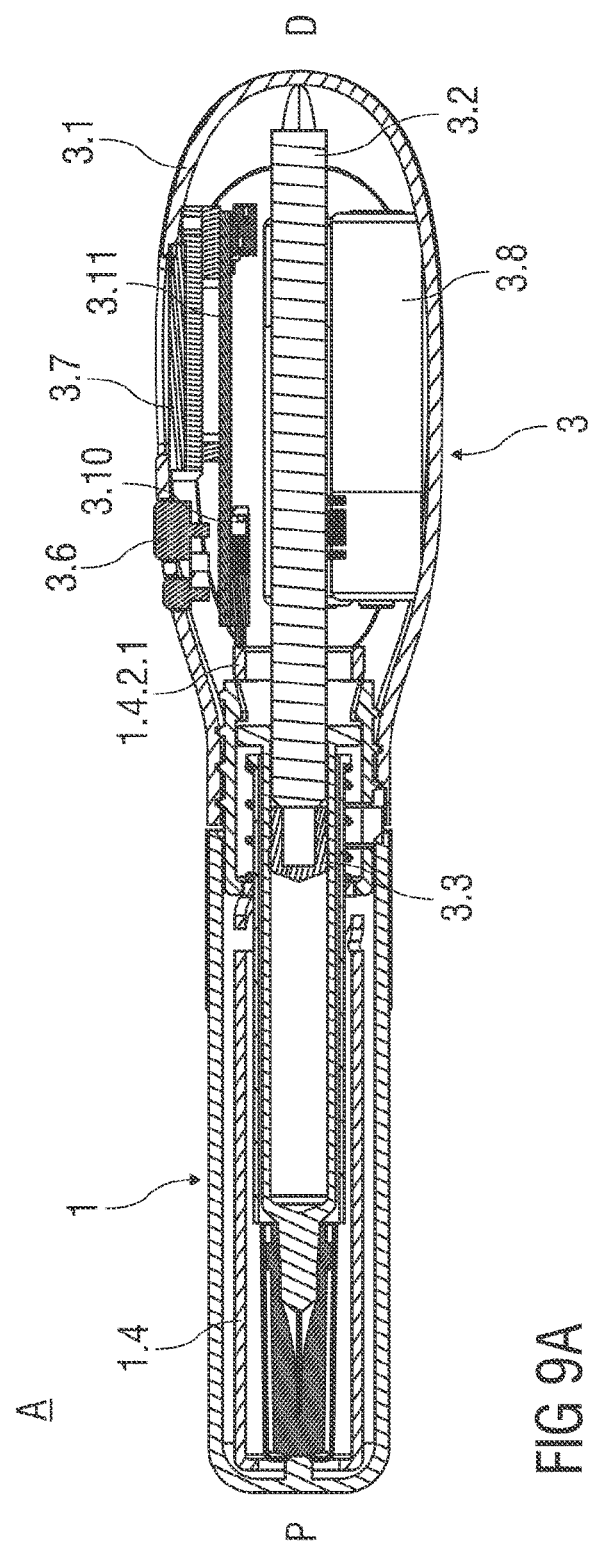
FIGS. 9A and 9B show two sectional views of the auto-injector according to the first embodiment of the invention.
Figure 9B:
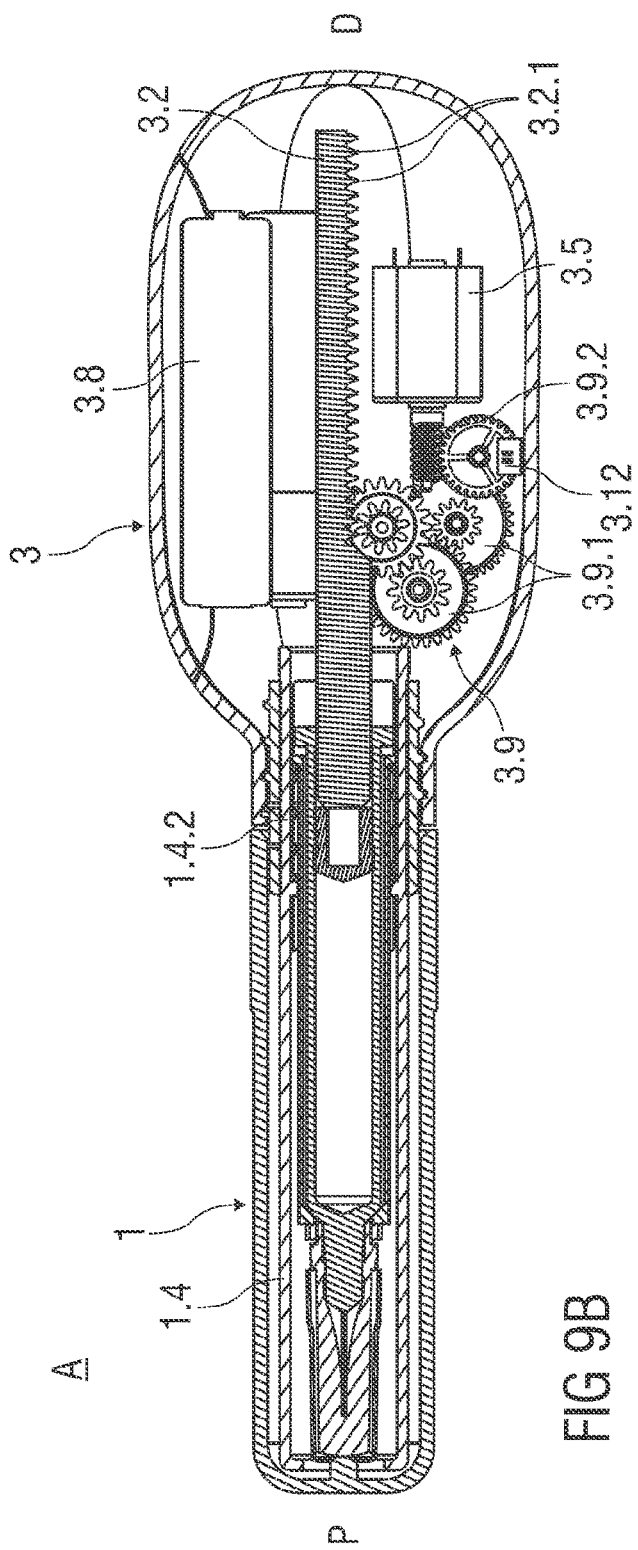

The substantially tubular front-end device 1 is attachable to a proximal end of a reusable back-end device 3 shown in more detail in FIGS. 9A and 9B. The back-end device 3 comprises driving means, like, in particular, an electric motor 3.5 of the auto-injector A.

Figure 2A:
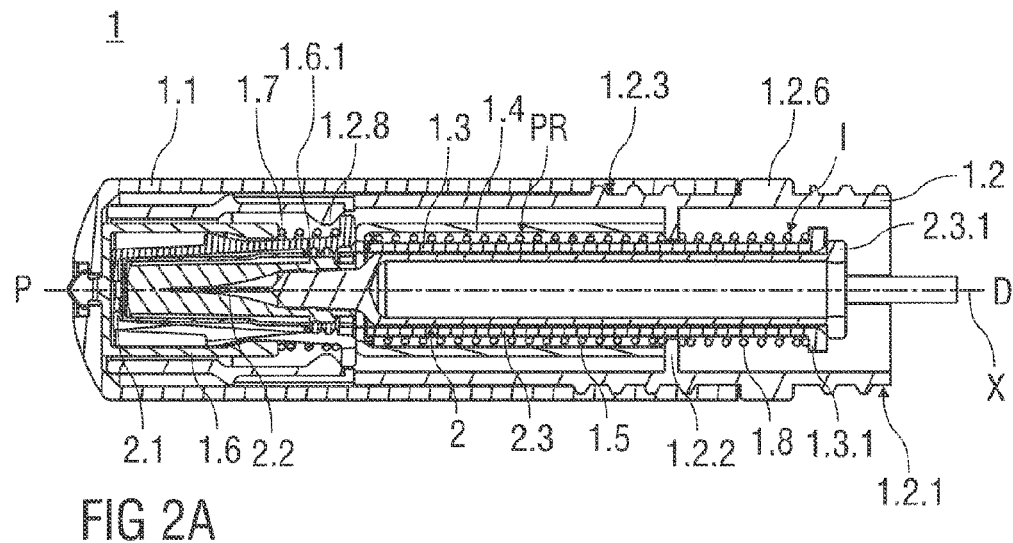
FIGS. 2A and 2B show sectional views of the reusable front-end device of the auto-injector according to the first embodiment of the invention with the syringe inserted into the front-end device.
Figure 2B:
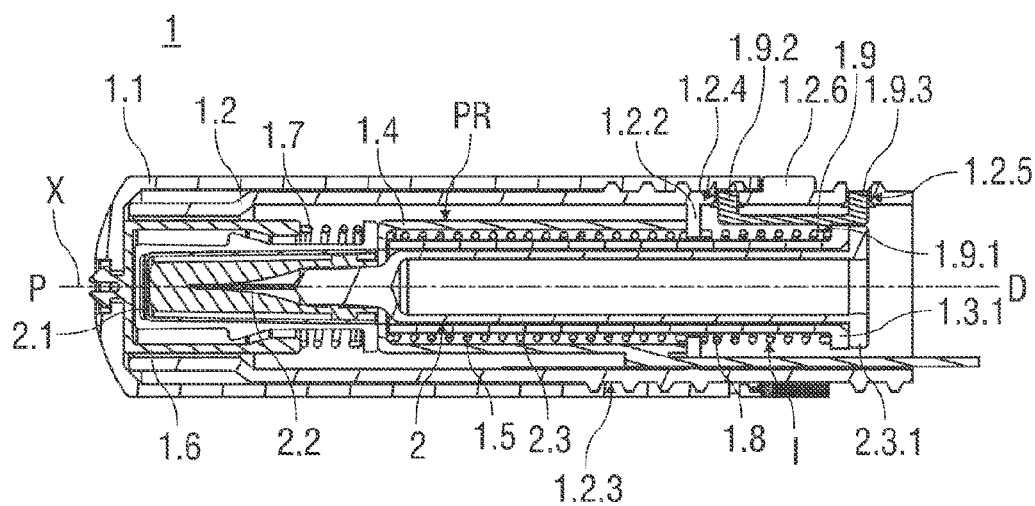

The front-end device 1 comprises a tubular outer sleeve 1.1 with a substantially closed proximal end, a tubular support sleeve 1.2 received within the outer sleeve 1.1 and a tubular syringe retainer 1.3 retained in the support sleeve 1.2. The syringe retainer 1.3 is adapted to receive and mount the pre-filled syringe 2, as shown in FIGS. 2A and 2B.

A first screw thread 1.2.1 disposed at the distal end of the support sleeve 1.2 provides a means for attaching the front-end device 1 to the back-end device 3. The first screw thread 1.2.1 may be arranged as a right hand screw thread, so that the back-end device 3 may be attached to the front-end device 1 by a clockwise rotation, viewed from the distal end of the back end device 3.

A substantially cylindrical needle shroud 1.4 is slidably arranged with respect to the syringe retainer 1.3 and surrounds a proximal section of the syringe retainer 1.3 in a retracted position PR. A pre-tensioned transfer spring 1.5 bears against an annular rib 1.2.2 formed to an inner surface of the support sleeve 1.2 in the distal direction D and against a shoulder 1.4.1 formed to a proximal end of the needle shroud 1.4 to bias the needle shroud 1.4 with respect to the support sleeve 1.2 in the proximal direction P.

The needle shroud 1.4 abuts against two clamp arms 1.6.1 arranged opposite to each other in the proximal direction P, so that the needle shroud 1.4 is retained in the retracted position PR against the biasing force provided by the transfer spring 1.5. The clamp arms 1.6.1 are inserted into a locking sleeve 1.6 firmly connected to the closed proximal end of the outer sleeve 1.1. As best seen in FIG. 1A, the two clamp arms 1.6.1 are splayed in the radial outward direction, so that a protective needle cap 2.1 attached to a proximal tip of the pre-filled syringe 2 may be easily inserted in the intermediate area between the two clamp arms 1.6.1.

A first ramp 1.6.2 is formed to an inner surface of the locking sleeve 1.6 that abuts against a correspondingly formed outward rib 1.6.3 on clamp arm 1.6.1, so that the clamp arms 1.6.1 are deflected radially inwards when the locking sleeve 1.6 is translated parallel to an axis X of the substantially cylindrical front-end device 1 in a proximal direction. A clamp spring 1.7 arranged between the locking sleeve 1.6 and the clamp arms 1.6.1 biases the locking sleeve 1.6 and the clamp arms 1.6.1 away from each other along axis X. The interaction of the first ramp 1.6.2 and the outward rib 1.6.3 redirects the biasing force provided by the clamp spring 1.7 in the radial inward direction. Thus, the clamp arms 1.6.1 are biased radially inwards. Inward movement of the clamp arms 1.6.1 is limited by the axial travel allowed for clamp spring 17.

The needle cap 2.1 may be gripped by the clamp arms 1.6.1 and pulled off the proximal tip of the pre-filled syringe 2 by inserting the pre-filled syringe 2 into the syringe retainer 1.3 and removing the outer sleeve 1.1 from the support sleeve 1.2 of the front-end device 1.

The outer sleeve 1.1 is connected to the support sleeve 1.2 by a second screw thread 1.2.3. The second screw thread 1.2.3 comprises a direction of rotation that is opposite to the one of the first screw thread 1.2.1. As the first screw thread 1.2.1 is designed as a right hand screw thread, the second screw thread 1.2.3 is arranged as a left hand screw thread.

Alternatively, the first screw thread 1.2.1 may be arranged as a left hand screw thread and the second screw thread 1.2.3 may be designed as a right hand screw thread. In this alternative embodiment, the back-end device 3 can be attached to the front-end device 1 by a counter-clockwise rotation.

A radially protruding support collar 1.2.6 is formed to the outer surface of the support sleeve 1.2 between the first screw thread 1.2.1 and the second screw thread 1.2.3. The support collar 1.2.6 acts as a bearing surface for both the first and the second screw thread 1.2.1, 1.2.3. Therefore, a proximal end of the back-end device 3 bears against the support collar 1.2.6 in the proximal direction P when the back-end device 3 is attached to the front-end device 1. Respectively, the outer sleeve 1.1 bears against the support collar 1.2.6 in the distal direction D when the outer sleeve 1.1 is screwed all the way in.

A return spring 1.8 bears against the annular rib 1.2.2 of the support sleeve 1.2 and against a first flange formed to the distal end of the syringe retainer 1.3. When the syringe retainer 1.3 is in a first position I shown in FIGS. 1A and 1B, the return spring 1.8 is in a relaxed or slightly compressed state. An axial translation of the syringe retainer 1.3 with respect to the support sleeve 1.2 in the proximal direction P compresses the return spring 1.8, so that the syringe retainer 1.3 is biased to return to the first position I. The axial translation of the syringe retainer 1.3 with respect to the support sleeve 1.2 in the proximal direction P requires prior removal of the outer sleeve 1.1.

FIG. 1B shows an assembly lock 1.9 arranged at the distal end of the support sleeve 1.2 that comprises a second inward projection 1.9.1. The assembly lock 1.9 comprises an essentially u-shaped cross-section and first and second locking pins 1.9.2, 1.9.3 that protrude into respective first and second orifices 1.2.4, 1.2.5 formed into the support sleeve 1.2. The assembly lock 1.9 is biased in the radial outward direction by a biasing means (not illustrated). The outer sleeve 1.1 screwed onto the support sleeve 1.2 abuts against the first locking pin 1.9.2 and pushes the assembly lock 1.9 radially inwards, so that the second inward projection 1.9.1 latches to the first flange 1.3.1 to prevent a proximal displacement of the syringe retainer 1.3 with respect to the support sleeve 1.2. The syringe retainer 1.3 may be arranged to be prevented from moving in the distal direction D from the first position I. For this purpose the second inward projection 1.9.1 may engage in a recess (not illustrated) in the first flange 1.3.1 or the second inward projection 1.9.1 may be arranged to wrap over the first flange 1.3.1 so as to retain the syringe retainer 1.3 in both directions until the front-end device 1 and the back-end device 3 are assembled together. A spring, e.g. in the shape of a clip may be provided for biasing the assembly lock 1.9 radially outwards.

FIGS. 2A and 2B show sectional views of the front-end device 1 with the pre-filled syringe 2 inserted into the syringe retainer 1.3. The needle cap 2.1 covers an injection needle 2.2 attached to a proximal end of the pre-filled syringe 2. The pre-filled syringe 2 comprises a barrel 2.3 containing the dose of the medicament or drug. A barrel collar 2.3.1 is formed to the distal end of the barrel 2.3 and abuts proximally against the first flange 1.3.1 of the syringe retainer 1.3.

The front-end device 1 may be loaded by inserting the pre-filled syringe 2 into the syringe retainer 1.3. This may be most easily, but not necessarily, achieved by orienting the front-end device 1 vertically. The needle cap 2.1 does not have to be removed before the pre-filled syringe 2 is inserted into the front-end device 1 to provide increased protection from accidental needle stick injuries. The initial radial spacing of clamp arms 1.6.1 is such that the needle cap 2.1 can pass fully between them. A first inward projection 1.2.8 is formed to an inner surface of the support sleeve 1.2 that abuts against the clamp arm 1.6.1. As the outer sleeve 1.1 is removed from the support sleeve 1.2 it draws with it the locking sleeve 1.6 and clamp arms 1.6.1. The first inward projection 1.2.8 directs the clamp arm 1.6.1 radially inwards, so that the needle cap 2.1 is firmly gripped by the clamp arms 1.6.1 and may be removed from the proximal tip of the pre-filled syringe 2 by removing the outer sleeve 1.1 from the support sleeve 1.2.

Figure 3:
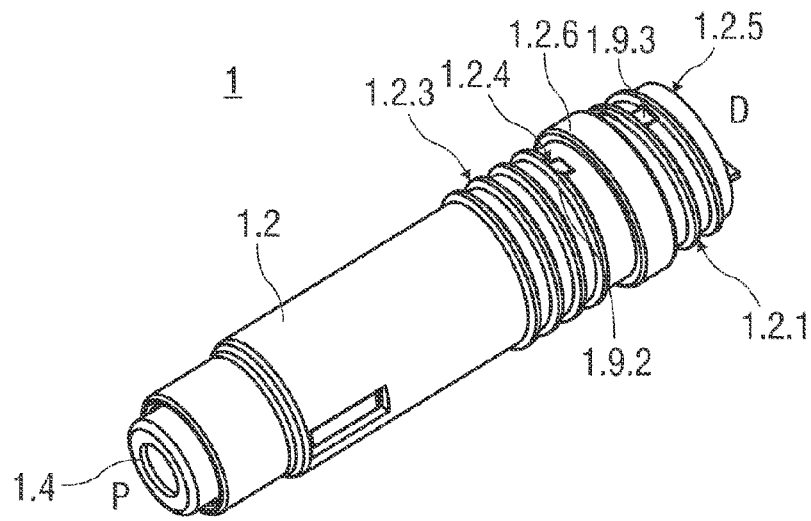
FIG. 3 shows a perspective view of the front-end device according to the first embodiment with the outer sleeve removed from a support sleeve.

FIG. 3 shows a perspective view of the front-end device 1 according to the first embodiment with the outer sleeve 1.1 removed from the support sleeve 1.2. The needle shroud 1.4 is in an advanced position PA and protrudes from the support sleeve 1.2 in the proximal direction P. The first locking pin 1.9.2 of the assembly lock 1.9 protrudes through the first orifice 1.2.4 of the support sleeve 1.2 and may be pushed inwards when the outer sleeve 1.1 is screwed onto the support sleeve 1.2. Respectively, the second locking pin 1.9.3 protrudes through the second orifice 1.2.5 and may engage the back-end device 3.

Figure 4A:
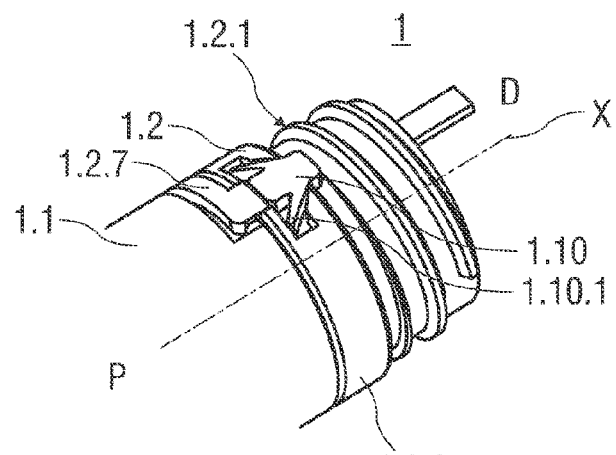
FIGS. 4A and 4B show details of the support sleeve of the front-end device according to the first embodiment in two perspective views.
Figure 4B:
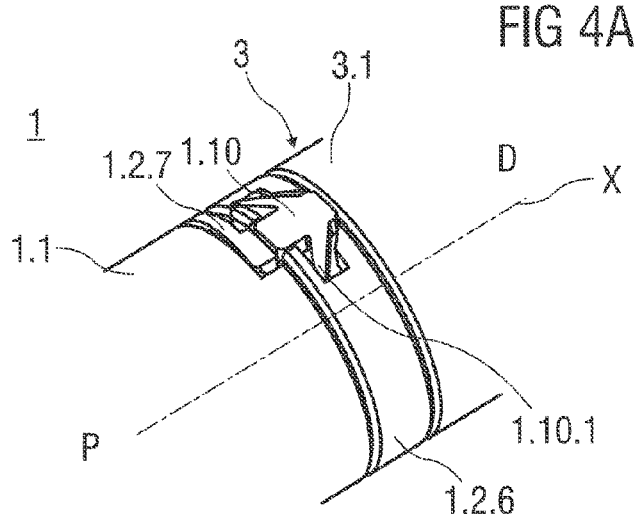

FIGS. 4A and 4B show details of the support sleeve 1.2 of the front-end device 1 in two perspective views. The outer sleeve 1.1 is screwed onto the support sleeve 1.2 and covers a proximal section thereof. A drive dog 1.10 is slidably arranged with respect to the support sleeve 1.2. Two spring arms 1.10.1 are formed to the drive dog 1.10 that bias the drive dog 1.10.1 in the distal direction D. The drive dog 1.10 is slidably mounted to the support collar 1.2.6 separating the first screw thread 1.2.1 and the second screw thread 1.2.3 that is engaged by the outer sleeve 1.1.

FIG. 4A shows the front-end device detached from the back-end device 3. The drive dog 1.10 protrudes from the support collar 1.2.6 in the distal direction D, so that the drive dog 1.10 may be axially translated in the proximal direction P when the back-end device 3 is attached to the front-end device 1 via the first thread connection 1.2.1. The drive dog 1.10 bears against a latch 1.2.7 formed to the distal end of the outer sleeve 1.1. When the front-end device 1 is detached from the back-end device, the latch 1.2.7 latches to the support collar 1.2.6 of the support sleeve 1.2 and rotationally affixes the outer sleeve 1.1 with respect to the support sleeve 1.2.

FIG. 4B shows the front-end device 1 according to the first embodiment attached to the back-end device 3 having a housing 3.1. The front-end device 1 is screwed all the way in, so that the proximal end of the housing 3 of the back-end device 3 pushes the drive dog 1.10 abutting against the latch 1.2.7 in the proximal direction P. The latch 1.2.7 disengages the support collar 1.2.6 and releases the rotational attachment of the support sleeve 1.2 with respect to the outer sleeve 1.1.

Figure 5A:
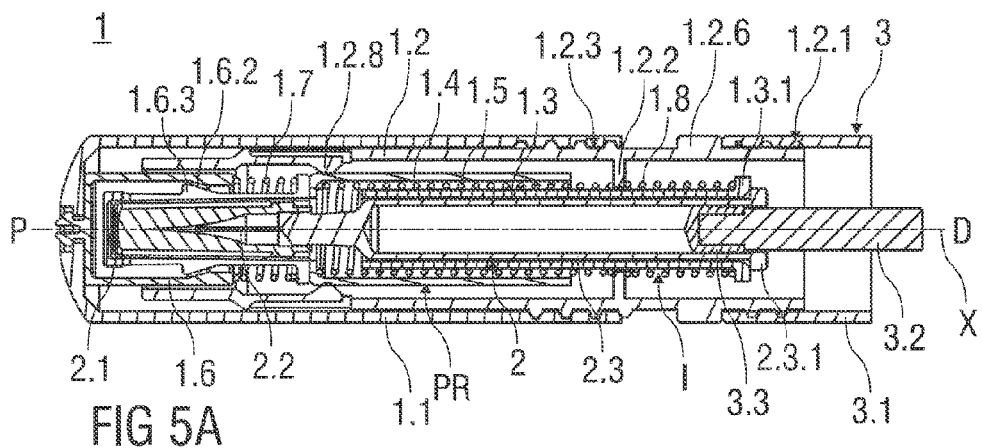
FIGS. 5A and 5B show sectional views of the front-end device according to the first embodiment that is connected to a reusable back-end device of the auto-injector.
Figure 5B:
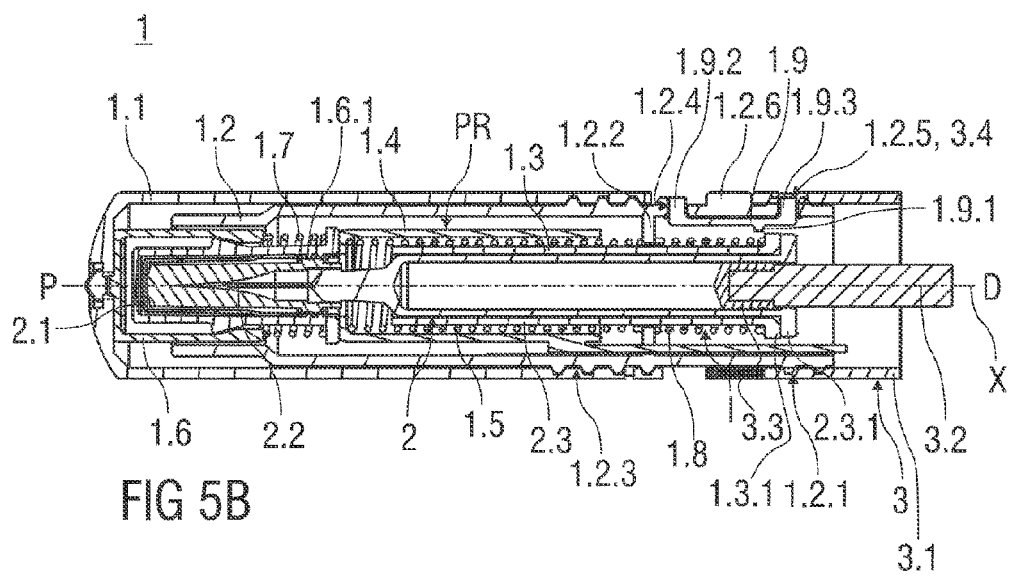

FIGS. 5A and 5B show sectional views of the front-end device 1 according to the first embodiment of the invention that is connected to the back-end device 3 via the first screw thread 1.2.1.

A plunger 3.2 of the back-end device 3 is connected to a stopper 3.3 that is inserted into a distal end of the barrel 2.3 of the pre-filled syringe 2. The stopper 3.3 seals the distal end of the barrel 3.2 in a fluid-tight manner. The plunger 3.2 and the stopper 3.3 may be axially displaced in the proximal direction P to expel the dose of the medicament contained in the pre-filled syringe 2 through the injection needle 2.2 during the injection.

The outer sleeve 1.1 is unscrewed and pulled off the support sleeve 1.2. The axial translation of the outer sleeve 1.1 with respect to the support sleeve 1.2 causes the clamp arms 1.6.1 to constrict in the radial inward direction and clamp to the needle cap 2.1.

Preferably, the needle cap 2.1 is made at least partially from a relative soft plastics material, so that the needle cap 2.1 may be easily gripped by the inwardly deflected clamp arms 1.6.1. The needle cap 2.1 may be arranged as a rubber needle shield or as a rigid needle shield. The rigid needle shield has two apertures in the outer rigid part which would allow the barbs on the clamp arms 1.6.1 to enter, gripping the needle cap 2.1 securely.

As illustrated in FIG. 5B, the proximal displacement of the outer sleeve 1.1 releases the assembly lock 1.9 that prevents a proximal movement of the syringe retainer 1.3 within the support sleeve 1.2. The outer sleeve 1.1 makes way for the first locking pin 1.9.2 of the assembly lock 1.9 to protrude through the first orifice 1.2.4. The assembly lock 1.9 is moved radially outwards, so that the second inward projection 1.9.1 disengages the first flange 1.3.1 to unlock the syringe retainer 1.3. The syringe retainer 1.3 may now move with respect to the support sleeve 1.2 in the proximal direction P.

The second locking pin 1.9.3 of the assembly lock 1.9 protrudes through the second orifice 1.2.5 of the support sleeve 1.2 and into a third orifice 3.4 formed into a proximal end section of the housing 3.1. The assembly lock 1.9 locks the support sleeve 1.2 to the housing 3.1 of the back-end device 3 in a manner to prevent a relative rotation of these parts 1.1, 3. Thus, the support sleeve 1.2 cannot be unscrewed from the back-end device 3 until the outer sleeve 1.1 is re-attached to the support sleeve 1.2.

The auto-injector A comprising the pre-filled syringe 2, the front-end device 1 and the back-end device 3 is assembled before an injection in a particularly simple manner. After the pre-filled syringe 2 is inserted in the syringe retainer 1.3 of the front-end device 1 with the outer sleeve 1.1 attached thereto, the outer sleeve 1.1 may be gripped by the user and the back-end device 3 is screwed onto the right-handed first screw thread 1.2.1 by a clockwise rotation. When the first screw thread 1.2.1 bottoms out, the drive dog 1.10 is axially translated in the proximal direction P and releases the latch 1.2.7. A continuous clockwise rotation of the back-end device 3 causes the outer sleeve 1.1 to rotate with respect to the support sleeve 1.2, whereby the left-handed second screw thread 1.2.3 is released.

Alternatively, the back-end device 3 is attachable to the front-end device 1 and the outer sleeve 1.1 is detachable from the support sleeve 1.2 by continuously rotating the back-end device 3 with respect to the outer sleeve 1.1 in a counter-clockwise direction. In this alternative embodiment of the invention, the first screw thread 1.2.1 is arranged as a left-handed screw connection, whereas the second screw thread 1.2.3 is right-handed.

Figure 6:
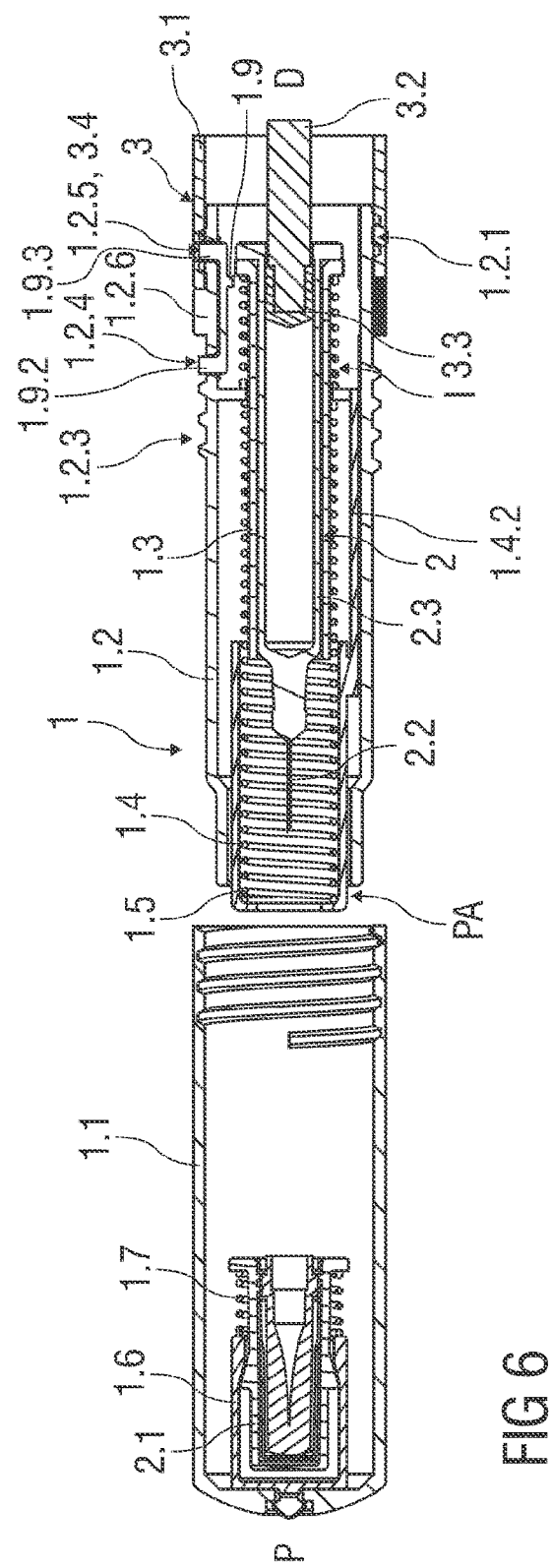
FIG. 6 shows a sectional view of the front-end device according to the first embodiment with the outer sleeve detached therefrom.

FIG. 6 shows a sectional view of the front-end device 1 attached to the back-end device 3 and detached from the outer sleeve 1.1. The needle cap 2.1 is gripped by the clamp arms 1.6.1 that are connected to the outer sleeve 1.1 via the locking sleeve 1.6. The first inward projections 1.2.8 direct the clamp arms 1.6.1 radially inwards to support the clamp arms 1.6.1 clamping to the needle cap 2.1. As the outer sleeve 1.1 is pulled off the support sleeve 1.2, the needle cap 2.1 is removed from the proximal tip of the pre-filled syringe 2.1 and the injection needle 2.2 is exposed. The clamp spring 1.7 maintains a radially inwards directed force upon the clamp arms 1.6.1, so that the needle cap 2.1 is retained within the detached outer sleeve 1.1.

Upon removal of the outer sleeve 1.1, the transfer spring 1.5 relaxes and moves the needle shroud 1.4 to the advanced position PA. In the advanced position PA, the needle shroud 1.4 protrudes from the support sleeve 1.2 in the proximal direction P. A proximal end of the needle shroud 1.4 is pushed towards the skin of the patient during the injection.

The needle shroud 1.4 comprises an extension arm 1.4.2 that is adapted to communicate an axial displacement of the needle shroud 1.4 to the back-end device 3. As illustrated in more detail in FIGS. 9A and 9B, a skin interlock shroud 1.4.2.1 may be formed to a distal end to the extension arm 1.4.2 that interacts with an interlock switch 3.10. The interlock switch 3.10 detects the displacement of the needle shroud 3.10 to determine if the needle shroud 1.4 is in contact with the skin of the patient. The back-end device 3 may comprise a mechanism that allows for an activation of the motor 3.5 only if the contact of the needle shroud 1.4 with the skin is detected.

Figure 7:
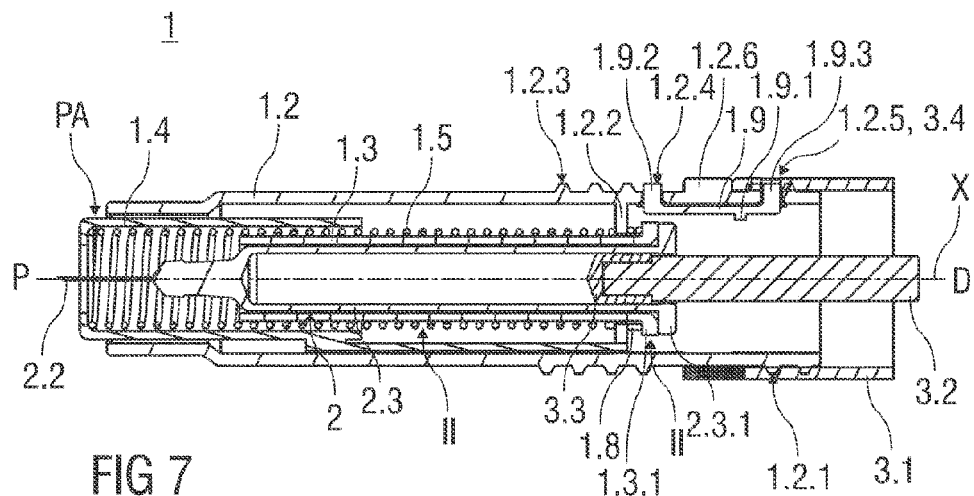
FIG. 7 shows a proximal section of the auto-injector comprising the front-end device according to the first embodiment and the back-end device in mid injection.

FIG. 7 shows a proximal section of the auto-injector A comprising the front-end device 1 and the back-end device 3 in mid injection. The needle shroud 1.4 is pushed against the skin of the patient and the reusable motor 3.5 of the back-end device is activated to drive the syringe retainer 1.3 and the pre-filled syringe 2 retained therein in the proximal direction P to a second position II, whereby the return spring 1.8 is compressed. The injection needle 2.2 protrudes from the needle shroud 1.4 proximally in the second position II and punctures the skin of the patient. A maximal penetration depth of the injection needle 2.2 is limited by the annular rib 1.2.2 that limits the proximal displacement of the syringe retainer 1.3 holding the pre-filled syringe 2 with respect to the support sleeve 1.2.

The stopper 3.3 connected to the plunger 3.2 is driven by the motor 3.5 of the back-end device 3 in the proximal direction P and depressed into the barrel 2.3 of the pre-filled syringe 2, whereby the dose of the medicament is expelled through the injection needle 2.2 and disposed beneath the skin of the patient.

Figure 8:
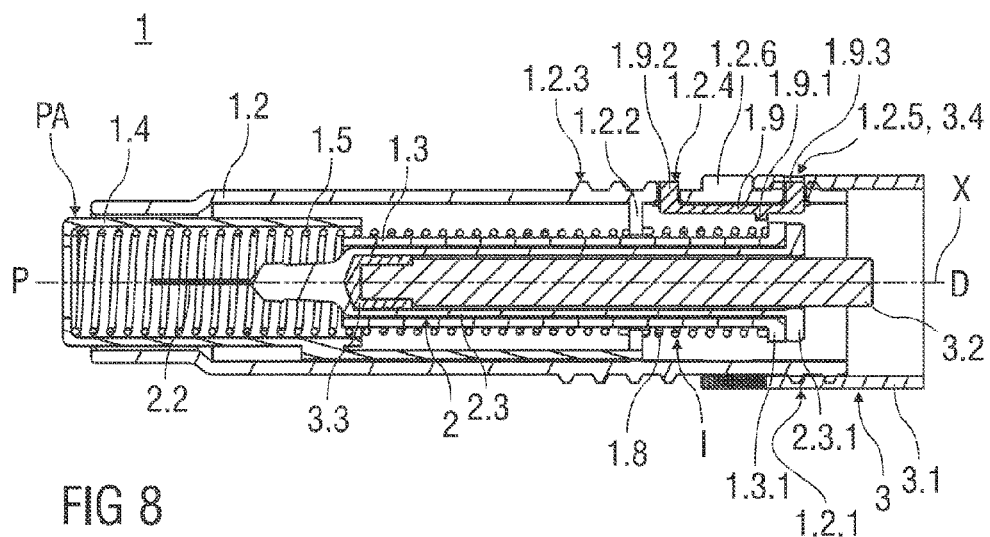
FIG. 8 shows the proximal section of the auto-injector comprising the front-end device according to the first embodiment and the back-end device after injection of the medicament.

FIG. 8 shows the proximal section of the auto-injector A according to the first embodiment comprising the front-end device 1 and the back-end device 3 after injection of the medicament. The plunger 3.2 has been released or actively withdrawn allowing retraction of the syringe 2. The compressed return spring 1.8 relaxes and drives the syringe retainer 1.3 back to the first position I, whereby the injection needle 2.2 of the syringe 2 is withdrawn from the skin of the patient.

Alternatively or additionally, the motor direction of the motor 3.5 is reversed to retract the syringe 2 and the syringe retainer 1.3 to the first position I.

The auto-injector A is then removed from the injection site. The assembly lock 1.9 is locked and prevents a relative rotation between the support sleeve 1.2 of the front-end device 1 and the housing 3.1 of the back-end device 3. Thus, the auto-injector A may not be disassembled until the outer sleeve 1.1 is screwed back onto the support sleeve 1.2 to unlock the assembly lock 1.1. This mechanism forces the user performing the injection to re-attach the needle cap 2.1 retained within the outer sleeve 1.1 onto the proximal tip of the syringe 2 after the injection, so that the injection needle 2.2 is covered when the syringe 2 is removed from syringe retainer 1.3 of the front-end device 1.

The outer sleeve 1.1 is re-attached to the support sleeve 1.2 as illustrated in FIGS. 5A and 5B. As the outer sleeve 1.1 is screwed onto the support sleeve 1.2, the inner surface of the outer sleeve 1.1 engages the first locking pin 1.9.2 protruding radially outwards through the first orifice 1.2.4 and pushes the assembly lock 1.9 radially inwards. The second locking pin 1.9.3 disengages the third orifice 3.4 formed into the housing 3 of the back-end device 3, so that the back-end device 3 is allowed to rotate relative to the support sleeve 1.2 and may be disassembled from the front-end device 1.

The clamp arms 1.6.1 connected to the outer sleeve 1.1 via the locking sleeve 1.6 bear against the needle shroud 1.4 in the distal direction D and push the needle shroud 1.4 back to the retracted position PR. The needle cap 2.1 slides back onto the proximal tip of the syringe 2 to re-sheathe the injection needle 2.2 after the injection.

As can be seen in FIGS. 2A and 2B, the front-end device 1 is detached from the back end-device 3 when the outer sleeve 1.1 engaging the second screw thread 1.2.3 is screwed all the way in. The needle shroud 1.4 in the retracted position PR bears against the clamp arms 1.6.1 in the proximal direction P and splays the clamp arms 1.6.1 radially outwards. The clamp arms 1.6.1 disengage the needle cap 2.1 that frictionally engages the proximal tip of the syringe 2 and covers the used injection needle 2.2. The empty syringe 2 may now be safely removed from the syringe retainer 1.3 of the re-useable front-end device 1 and disposed. The clamp arms 1.6.1 may be integrally moulded in a radially outward position so they would not need to be splayed apart but just allowed to relax towards their radial outward position. The clamp arms 1.6.1 may likewise be made from spring steel or an additional spring could be provided for splaying them apart.

FIGS. 9A and 9B show sectional views of the assembled auto-injector A comprising a similar front-end device 1, the syringe 2 and the back-end device 3. The cross-section shown in FIG. 9A extends perpendicularly to the one shown in FIG. 9B. The housing 3.1 of the back-end device 3 comprises substantially oval cross-sections of different dimensions.

The reusable back-end device 3 of the auto-injector A comprises a plurality of control elements 3.6 used to activate and control a variety of features of the auto-injector A, such as activating and de-activating the electric motor 3.5 that axially translates the plunger 3.2 to insert and/or retract the injection needle 2.2 and to inject the dose of the medicament. Furthermore, the speed of the needle insertion or the penetration depth of the injection needle 2.2 may be controlled and/or time delays may be introduced by the user. The back-end device 3 may be provided with a variety of user-selectable speed profiles that control the torque provided by the motor to facilitate the needle insertion process and/or to modify the injection speed. Various parameters may be modified to suit the user and/or to drug requirements, like the viscosity of the medication.

The back-end device 3 may comprise a memory unit (not illustrated) that may be used to store user related data for compliance monitoring. If the patient is on a medication, the back-end device 3 can be used to monitor that the dose of the medicament is administered at correct regular intervals. Furthermore, a set of device specification parameters may be stored in the memory unit. The specification parameters may be compared with actual parameters determined during use of the auto-injector A. For example, the force needed to insert the injection needle 2.2 into the skin is characterized by the current measured during the needle insertion process. If the measured current is out of specification, the back-end device 3 detects an incorrect use of the auto-injector A and may abort the injection. Another possible application includes comparing the initial position of the stopper 3.3 with a corresponding specification parameter at the beginning of the injection. If the position of stopper 2.5 is out of specification, the back-end device 3 detects that a used and empty syringe 2 is loaded to the front-end device 1 and may disable the injection mechanism to prevent injuries. The auto-injector A may fail to operate when no syringe 2 is inserted into the syringe retainer 1.3.

The back-end device 3 has a display 3.7, preferably a liquid crystal display (LCD), that may visually display injection progress, injection completion, historical user data and/or drug properties, like an expiry date. The display 3.7 may display messages to remind the patient to take his medicament, specification parameters, an operation mode and/or the type of the medicament contained in the pre-filled syringe 2. Additionally or alternatively, the back-end device 3 may comprise adequate means to provide an acoustic and/or haptic feedback to the patient and/or the user of the auto-injector A.

The back-end device 3 may comprise a sensor unit (not illustrated) capable of detecting actual parameters, like the type of medicament or drug contained in the pre-filled syringe 2 in particular by means of radio frequency identification (RFID) or barcode reading. This allows for an automatic configuration of the auto-injector A to properties of the medicament. For example, the penetration depth of the injection needle 2.2 may be automatically adapted to a depth as required by the medicament. The auto-injector A is particularly suited to be used for administering a variety of drugs that may require an intradermal, a transcutaneous or an intramuscular injection.

Additional sensor units (not illustrated) may be arranged in particular as micro switches that detect the correct assembly of the auto-injector A and/or the correct mounting of the front-end device 1 to the back-end device 3. The sensor units may also be arranged as encoders, light gates and/or current monitoring systems.

The motor 3.5 of the auto-injector A is powered by an energy supply 3.8 that may be provided by a set of rechargeable or disposable batteries. The torque provided by the motor 3.5 is transferred to the plunger 3.2 by a gearbox 3.9 comprising, typically, a plurality of gearwheels 3.9.1 and a worm gear 3.9.2. A plurality of gear teeth 3.2.1 are formed to the plunger 3.2 that are engaged by one of the gearwheels 3.9.1 to convert the rotational motion to a linear motion of the plunger 3.2 as in a rack and pinion gear pair. The gearbox 3.9 in particular increases the output torque transferred to the plunger 3.2 to deliver the required plunger motion and force.

Alternative back-end devices 3 may be arranged without a gearbox. Other forms of gearboxes may likewise be applied—eg a lead screw driven directly or indirectly by the motor. Other motors with built in gear boxes or linear motors may also be used.

A distal displacement of the interlock shroud 1.4.2.1 connected to the needle shroud 1.4 may be detected by the interlock switch 3.10. The detected distal position PA, PR of the needle shroud 1.4 indicates whether or not the auto-injector A is correctly placed onto the skin of the patient so that the dose of medication may be injected. The back-end device 3 may be programmed in a manner that allows for an activation of the motor 3.5 only if the needle shroud 1.4 is in contact with the skin of the patient. Furthermore, the direction of the motor 3.5 may be immediately inverted when the auto-injector A is removed from the injection site at any time of the injection allowing for a partial delivery of the dose of the medicament. Upon removal of the auto-injector A from the injection site, the injection needle 2.2 is retracted to reduce the risk of an accidental needle stick. Removal from the injection site may be detected by the needle shroud 1.4 returning into the advanced position PA.

An electronic control unit 3.11 is arranged within the housing 3.1 that controls the various features of back-end device 3 and in particular the motor 3.5. The electronic control unit 3.11 may comprise a printed circuit board (PCB). A closed loop motion control may be embedded in the electronic control unit 3.11 that controls the speed of the motor 3.5 to reduce shock loads on the reusable auto-injector A and/or on the syringe 2 and hence reduce the risk of breaking the syringe 2.

The electronic control unit 3.11 is capable of detecting a stall of the motor 3.5 at the end of the injection stroke delivering the dose of medication to the patient. This indicates that the syringe 2 is completely empty and may trigger the needle retraction mechanism of the auto-injector A.

An encoder sensor 3.12 capable of determining the position of the plunger 3.2 is connected to the gearbox 3.9. Detection of the position of the plunger 3.2 is used to achieve a phased motion of the plunger 3.2 during the injection. Hence, the translation speed of the plunger 3.2 may be adapted to the different phases of the drug delivery comprising the needle insertion phase, the expelling of the medicament and the needle retraction phase. Needle insertion is thought to be less painful to the patient when performed quickly whereas injection is considered less painful when performed rather slowly.

Although the back-end device 3 in the above described embodiment of the front-end 1 is motor driven, the front-end device 1 may likewise be combined with back-end devices having different thrust means such as a compression spring, a torsion spring, a gas spring or a combustion engine.

The above described back-end device 3 may likewise be combined with a disposable front-end device which is completely discarded after use. Although the re-usable front-end device 1 requires fewer resources and produces less waste, the disposable front-end device avoids the risk of cross contamination since none of its components will get in contact with more than one patient.

The arrangement comprising the locking sleeve 1.6, the clamp arms 1.6.1, the first inward projection 1.2.8 and the clamp spring 1.7 described above is not limited to being used in this embodiment. It may likewise be used for removing and replacing the needle cap 2.1 or protective needle sheath in other re-usable or disposable front-end devices, re-usable or disposable auto-injectors or manually operated injection devices. The locking sleeve 1.6 may be attached to an outer sleeve 1.1 or device cap for joint translation. The connection between the locking sleeve 1.6 and the outer sleeve 1.1 may be arranged to allow relative rotation so as to avoid rotation of the needle cap 2.1 during removal when the outer sleeve 1.1 is rotated. The locking sleeve 1.6 may likewise be arranged to protrude from the device in a manner to allow a user to grip it for removal and replacement. In this case an outer sleeve 1.1 or device cap would not be required.

The invention claimed is:

1. A front-end device of an auto-injector (A) for administering a dose of a liquid medicament, comprising
a support sleeve with a first screw thread adapted to engage a housing of a back-end device of the auto-injector (A) to attach the front-end device to the back-end device and
an outer sleeve mounted onto a support sleeve of the front-end device by a second screw thread,
wherein the front-end device is adapted to receive a syringe with an injection needle and a barrel containing the dose of the medicament and wherein the direction of rotation of the first screw thread is opposite to the direction of rotation of the second screw thread, and
wherein a support collar separates the first screw thread from the second screw thread and a latch formed to the outer sleeve is arranged to latch to the support collar of the support sleeve to initially prevent a relative rotation between the outer sleeve and the support sleeve.

2. The front-end device according to claim 1, wherein a syringe retainer adapted to receive the pre-filled syringe is slidably arranged with respect to the support sleeve between a first position (I) with the needle covered inside the support sleeve and a second position (II) with the needle exposed for injection, wherein the outer sleeve is arranged to abut against an assembly lock that comprises a second inward projection arranged to latch to a first flange of the syringe retainer to prevent an axial translation of the syringe retainer in the first position (I) towards the second position (II).

3. The front-end device according to claim 2, wherein an annular rib is formed to the support sleeve to limit the axial translation of the syringe retainer in the proximal direction (P) so as to limit a maximal penetration depth of the injection needle.

4. The front-end device according to claim 1, wherein a drive dog is slidably mounted to the support collar and is arranged to abut against the latch, wherein the drive dog is arranged to be engaged by the housing of the back-end device when attached to the support sleeve via the first screw thread and wherein the latch is adapted to be translated by the drive dog engaged by the housing to disengage from the support collar.

5. The front-end device according to claim 1, wherein the outer sleeve is connected to at least one clamp arm adapted to clamp to a needle cap covering the injection needle.

6. The front-end device according to claim 5, wherein the clamp arm is biased by a clamp spring radially inwards to retain the needle cap within the outer sleeve when the outer sleeve is detached from the support sleeve.

7. The front-end device according to claim 1, wherein a needle shroud adapted to rest on the skin of a patient is slidably arranged with respect to the support sleeve, wherein the needle shroud comprises an extension arm adapted to communicate an axial displacement of the needle shroud to the back-end device of the auto-injector (A).

8. An auto-injector (A) for administering a dose of a liquid medicament, comprising:
a substantially tubular and reusable front-end device comprising:
a support sleeve with a first screw thread adapted to engage a housing of a back-end device of the auto-injector (A) to attach the front-end device to the back-end device and
an outer sleeve mounted onto a support sleeve of the front-end device by a second screw thread,
wherein the front-end device is adapted to receive a syringe with an injection needle and a barrel containing the dose of the medicament and wherein the direction of rotation of the first screw thread is opposite to the direction of rotation of the second screw thread, and
wherein a support collar separates the first screw thread from the second screw thread and a latch formed to the outer sleeve is arranged to latch to the support collar of the support sleeve to initially prevent a relative rotation between the outer sleeve and the support sleeve; and
a reusable back-end device comprising:
a housing,
a plunger connected to or adapted to engage a stopper providing a fluid tight seal for a distal end of the barrel,
a motor for displacing the plunger,
wherein the front-end device is attached to the housing via the first screw thread and the outer sleeve is mounted onto the support sleeve of the front-end device by a second screw thread, wherein the direction of rotation of the first screw thread is opposite to the direction of rotation of the second screw thread.

9. The auto-injector (A) according to claim 8, wherein the outer sleeve is arranged to abut against an assembly lock that comprises a second inward projection arranged to latch to a first flange of the syringe retainer to prevent an axial translation of the syringe retainer in the first position (I) towards the second position (II), wherein the outer sleeve is arranged to release the assembly lock upon removal of the outer sleeve from the support sleeve, wherein, upon release, the assembly lock is capable of locking the support sleeve to the housing so as to prevent a relative rotation between the support sleeve and the housing.

10. The auto-injector (A) according to claim 8, wherein the assembly lock comprises a first locking pin and a second locking pin, wherein the first locking pin protrudes into a first orifice formed into the support sleeve and the second locking pin protrudes through a second orifice formed into the support sleeve and into a third orifice formed into the housing to prevent the relative rotation between the support sleeve and the housing.

11. The auto-injector (A) according to claim 8, wherein a needle shroud adapted to rest on the skin of a patient is slidably arranged with respect to the support sleeve, wherein an interlock switch is arranged within the back-end device capable of detecting an axial displacement of the needle shroud.

12. The auto-injector (A) according to claim 8, wherein the back-end device comprises a sensor unit for detecting actual parameters of the injection, a memory unit for storing user related data and/or specification parameters and a means to provide a visual, acoustic and/or haptic feedback to the user of the auto-injector (A).

13. The auto-injector (A) according to claim 8, wherein the back-end device further comprises an encoder sensor capable of determining the position of the plunger.

* * * * *